United States Patent [19]

Korczak et al.

[11] Patent Number: 4,762,950

[45] Date of Patent: Aug. 9, 1988

[54] SELECTIVE OXYALKYLATON OF N-(2-HYDROXYALKYL)-ANILINE

[75] Inventors: Alexander Korczak, Grosse Ile; William W. Levis, Jr., Wyandotte, both of Mich.

[73] Assignee: BASF Corporation, Parsippany, N.J.

[21] Appl. No.: 809,252

[22] Filed: Dec. 16, 1985

[51] Int. Cl.$^4$ .............................................. C07C 89/02
[52] U.S. Cl. ..................... 564/399; 564/443; 521/164; 252/182.12
[58] Field of Search ................ 564/399, 443; 521/164; 252/182, 188.31

[56] References Cited

U.S. PATENT DOCUMENTS

| | | | |
|---|---|---|---|
| 3,134,755 | 5/1964 | Müller et al. | 564/399 X |
| 3,154,535 | 10/1964 | Graham | 564/399 X |
| 4,562,290 | 12/1985 | Korczak et al. | 564/399 |

*Primary Examiner*—Paul F. Shaver
*Attorney, Agent, or Firm*—John C. Demeter; Joseph D. Michaels

[57] ABSTRACT

The subject invention relates to compositions prepared by oxyalkylation of N-(2-hydroxyalkyl)-aniline as the initiator compound with one or more alkylene oxides at elevated temperatures and in the presence of an alkali metal hydroxide. The resulting compositions have an unsymmetric structure with two functional groups, a secondary amino nitrogen and a hydroxyl group. The initiator compound reacts completely and removal of any residual initiator from the polyol is not required. When the subject invention polyol composition is reacted with an isocyanate, both urea and urethane groups form. The subject polyols may be used in the preparation of polyurethane products as well as nonionic and ionic surfactants.

6 Claims, No Drawings

SELECTIVE OXYALKYLATON OF N-(2-HYDROXYALKYL)-ANILINE

BACKGROUND OF THE INVENTION

1. Field of the Invention

The subject invention relates to low viscosity aromatic compositions prepared by oxyalkylation of N-(2-hydroxyalkyl)-aniline. The subject compositions may be used in the preparation of polyurethane products, as well as nonionic and ionic surfactants.

2. Description of the Prior Art

Alkylene oxide adducts of various aromatic amines are well known in the art. It is also known that such adducts are useful in the preparation of polyurethane products and as surfactants.

Generally, alkylene oxide adducts of aromatic amines are prepared by reacting an alkylene oxide with a aromatic amine at temperatures in excess of 100° C. in the presence of a alkoxylation catalyst. It is also known that aniline can be used as an initiator compound with one or more alkylene oxides.

SUMMARY OF THE INVENTION

The subject invention relates to compositions prepared by oxyalkylation of N-(2-hydroxyalkyl)-aniline with one or more alkylene oxides at elevated temperatures and in the presence of an alkali metal hydroxide catalyst. These reaction conditions result in compositions having an unsymmetric structure. The compositions have two functional groups, a secondary amino nitrogen and a hydroxyl group. The subject compositions have surprisingly low viscosity, generally less than 300 cps. It could not be predicted that compositions prepared by oxyalkylation of N-(2-hydroxyalkyl)-aniline would result in a low viscosity aromatic amine which is useful in the preparation of polyurethane products, such as rigid foams as well as nonionic and ionic surfactants.

As an initiator compound N-(2-hydroxyalkyl)-aniline is completely reacted and thus removal of any residual initiator from the crude polyol is not required. This is unlike the situation in which aniline is the initiator compound. The advantages inherit in the use of N-(2-hydroxyalkyl)-aniline as the initiator compound in the preparation of the polyurethane products includes cost and labor savings, as well as improved foam properties.

DESCRIPTION OF THE PREFERRED EMBODIMENTS

The alkylene oxide adducts of N-(2-hydroxyalkyl)-aniline are prepared, as previously stated, by reacting N-(2-hydroxyalkyl)-aniline with one or more alkylene oxides in the presence of an alkali metal hydroxide catalyst at temperatures of preferably at least 100° C. Those skilled in the art will know what equipment is needed and what precautions are necessary for preparing the subject compositions. A detailed explanation, therefore, of the process is not provided.

The alkali metal hydroxide catalysts preferred are potassium or sodium hydroxide. This is primarily due to cost and availability considerations. The amount of catalyst generally used should be about in a range of 0.4–5 percent based on total charge. A preferred range is about 4.5 percent to about 5 percent.

The preferred alkylene oxides are either propylene oxide, ethylene oxide or mixtures of both oxides. The alkylene oxides may be added individually or as mixtures to form heteric, blocked or mixed polymers. The mole ratio of alkylene oxide to N-(2-hydroxyalkyl)-aniline is in a range of 0.5 to 50 but is preferably from 2 to 10.

Preferred N-(2-hydroxyalkyl)-anilines include 2-hydroxylethyl aniline, 2-hydroxypropyl aniline, and mixtures thereof.

The reaction takes place at temperatures of at least 140° C. Generally, however it is preferred to use temperatures of at least 150° C. in order to produce the compositions with the desired viscosity.

The reaction utilizing as an initiator compound, N-(2-hydroxyalkyl)-aniline, proceeds to completion without need to remove any unreacted aniline by distillation from the crude polyol. This is a distinct advantage over prior art methods to prepare similar polyols. Removal of unreacted aniline is expensive in labor and in costs and can be dangerous as well as expensive.

Methods used for preparing polyurethane foams using the subject compositions are well known to one skilled in the art. As was previously indicated, the compositions may be used as nonionic and ionic surfactants and in the preparation of polyurethane products. Particularly due to two functional groups, a secondary amino hydrogen and a hydroxyl group the compositions may be used as chain-extending agents. It also possible to blend these polyols with higher viscosity polyols which would not normally be acceptable for the preparation of polyurethane products. The resulting blend would have an acceptable viscosity for foam production.

Polyurethane products are prepared from the subject compositions, or blend of the subject compositions, and customarily used polyols, by reacting them with an organic polyisocyanate. When so reacted, urea and urethane groups are formed. This results in polyurethane products with improved foam properties.

Organic polyisocyanates which can be used to prepare the polyurethane products are those customarily used and may be represented by the following formula:

wherein R″ is a polyvalent organic radical which is either aliphatic, aralkyl, alkylaryl, aromatic or mixtures thereof, and z is an integer which corresponds to the valence of R″ and is at least 2. Representative of the organic polyisocyanates contemplated herein includes, for example, aromatic diisocyanates such as 2,4-toluene diisocyanate, 2,6-toluene diisocyanate, mixtures of 2,4- and 2,6-toluene diisocyanate, crude toluene diisocyanate, diphenylmethane diisocyanate, crude diphenylmethane diisocyanate and the like; aromatic triisocyanates such as 4,4′,4″-tri-phenylmethane triisocyanate, 2,4,6-toluene triisocyanates; aromatic tetraisocyanates such as 4,4′-dimethyldiphenylmethane-2,2′,5,5′-tetraisocyanate, and the like; aralkyl polyisocyanates such as xylene diisocyanate, aliphatic polyisocyanates such as hexamethylene-1,6-diisocyanate, lysine diisocyanate methylester and the like, and mixtures thereof. Other organic polyisocyanates include hydrogenated methylene diphenylisocyanate, m-phenylene diisocyanate, naphthalene-1,5-diisocyanate, 1-methoxyphenylene-2,4-diisocyanate, 4,4′-biphenylene diisocyanate, 3,3′-dimethoxy-4,4′biphenyl diisocyanate, 3,3′-dimethyl-4,4′-biphenyl diisocyanate and 3,3′-dimethyldiphenylmethane-4,4′-diisocyanate. These polyisocyanates are prepared by conventional methods known in the art such as the phosgenation of the corresponding organic amine. Included within the usable isocyanates are modifications of the above isocyanates which contain carbodiimide, allophanate or isocyanurate structures. Quasi-prepolymers may also be employed in the process of the subject invention. These quasi-prepolymers are prepared by reacting an excess of organic polyisocyanate or mixtures thereof with a minor amount of an active hydrogen-containing compound as determined by the well-known Zerewitinoff test, as described by Kohler in *Journal of the American Chemical Society*, Vol. 49, page 3181 (1927). These compounds and their methods of preparation are well known in the art. The use of any one specific active hydrogen compound is not critical hereto, rather any such compound can be employed herein. Generally, the quasi-prepolymers have a free isocyanate content of from 20 percent to 40 percent by weight.

As was indicated previously, the organic polyisocyanate is reacted with the subject compositions or blends of the subject compositions and polyols customarily used. By "polyols customarily used" is meant polyols such as hydroxyl-terminated polyesters; polyoxyalkylene polyether polyols, alkylene oxide adducts of organic compounds having at least 2 reactive hydrogen atoms such as amines, and thiols; and hydroxy-terminated acetals.

Any suitable hydroxy-terminated polyester may be used such as are obtained, for example, from the reaction of polycarboxylic acids of polycarboxylic acid anhydrides and polyhydric alcohols. Any suitable polycarboxylic acid may be used in the preparation of hydroxy-terminated polyesters such as succinic acid, glutaric acid, adipic acid, pimelic acid, suberic acid, azelaic acid, sebacic acid, brassylic acid, thapsic acid, maleic acid, fumaric acid, glutaconic acid, $\alpha$-hydromuconic acid, $\beta$-butyl-$\alpha$-ethyl-glutaric acid, $\alpha,\beta$-diethylsuccinic acid, phthalic acid, isophthalic acid, terephthalic acid, hemimellitic acid, and 1,4-cyclohexanedicarboxylic acid. Anhydrides such as phthalic, tetrachlorophthalic, tetrabromophthalic, maleic, and 1,4,5,6,7,7-hexachloro-bicyclo-(2,2,1)-5-heptane-2,3-dicarboxylic acid anhydride also may be used in the preparation of the hydroxy-terminated polyesters. Any suitable polyhydric alcohol, including both aliphatic and aromatic, may be reacted with the polycarboxylic acid or polycarboxylic acid anhydride to prepare the hydroxy-terminated polyesters. Representative examples include ethylene glycol, 1,3-propanediol, 1,2-propane glycol, 1,4-butanediol, 1,3-butanediol, 1,2-butane glylcol, 1,5-pentanediol, 1,4-pentanediol, 1,3-pentanediol, 1,6-hexanediol, 1,7-heptanediol, 2-butene-1,4-diol glycerol, 1,1,1-trimethylolpropane, 1,1,1-trimethylolethane, hexane-1,2,6-triol, 60-methyl glucoside, pentaerythritol, and sorbitol. Also included with the term "polyhydric alcohol" are compounds derived from phenolic compounds such as 2,2-bis(4-hydroxyphenyl)propane, commonly known as Bisphenol A and hydroxyalkyl ethers of such phenolic compounds such as bis-2-hydroxyethyl ether of hydroxyquinone, and the alkylene oxide adducts of the above-named polyhydric alcohols.

The hydroxy-terminated polyester may also be a polyester amide such as is obtained by including some amine or amino alcohol in the reactants for the preparation of the polyesters. Thus, polyester amides may be obtained by condensing an amino alcohol such as ethanolamine with the polycarboxylic acids set forth above, or they may be made using the same components that make up the hydroxy-terminated polyester with only a portion of the components being a diamine such as ethylenediamine. The hydroxy-terminated polyester may also be a hydroxy-terminated polycaprolactone polyol.

Polyoxyalkylene ether polyols are preferably used as the polyol. These compounds are prepared by reacting an alkylene oxide with a polyhydric alcohol. Any suitable polyhydric alcohol may be used in the preparation of the polyoxyalkylene polyether polyol, such as those disclosed above for use in the preparation of the hydroxy-terminated polyesters. Any suitable alkylene oxide may be reacted with the polyhydric alcohol to prepare the polyoxyalkylene polyol. Representative examples include ethylene oxide, propylene oxide, butylene oxide, amylene oxide, styrene oxide, or mixtures thereof. Polyoxyalkylene polyols derived from two or more oxides may possess either block or heteric structure. In addition to polyoxyalkylene polyols, other compounds such as polyols derived from tetrahydrofuran and alkylene oxide-tetrahydrofuran mixtures may be used. The polyoxyalkylene polyether polyols preferably have primary hydroxyl groups, but may have secondary hydroxyl groups, and preferably, are polyethers prepared from alkylene oxides having from two to six carbon atoms such as polyethylene ether glycols, polyoxypropylene ether glycols and polyoxybutylene ether glycols. The polyoxyalkylene polyether polyols may be prepared by any known process such as, for example, the process disclosed by Wurtz in 1859 and in *Encyclopedia of Chemical Technology*, Vol. 7, pp. 257–262, published by Interscience Publishers, Inc. (1951), or the process disclosed in U.S. Pat. No. 1,922,459. Alkylene oxide adducts of Mannich condensation products are also useful in the invention.

In addition to the polyoxyalkylene polyether polyols just described, graft polyoxyalkylene polyether polyols may also be used in the preparation of the reactive polyol composition. These polyols are prepared by the in situ polymerization of a vinyl monomer or monomers in a reactive polyol medium and in the presence of a free radical initiator. The reaction is generally carried out at a temperature ranging from about 40° C. to 150° C. A more comprehensive discussion of the graft polyols and their method of preparation can be found in U.S. Pat. Nos. 4,208,314; 3,383,351 (Re. 28,715); 3,304,273; 3,652,639; and 3,823,201 (Re. 29,014).

As was previously mentioned, other suitable polyols which can be used in the reactive polyol composition of this invention include the alkylene oxide adducts of organic compounds having at least 2 active hydrogens, such as amines and thiols. The alkylene oxides which are useful in this regard are the same as those described in connection with the preparation of polyoxyalkylene polyether polyols.

Suitable thiols which may be reacted with an alkylene oxide include alkane thiols containing at least two —SH groups such as 1,2-ethanedithiol, 1,2-propanedithiol, 1,3-propanedithiol, and 1,6-hexanedithiol; and alkene-thiols such as 2-butene-1,4-dithiol, and alkynethiols such as 3-hexyne-1,6-dithiol.

Suitable polyamines which can be reacted with an alkylene oxide include aromatic polyamines such as methylene dianiline, polyaryl-polyalkylene polyamine (crude methylene dianiline), p-aminoaniline, 1,5-diaminonaphthalene, and 2,4-diaminotoluene; aliphatic polyamines such as ethylenediamine, 1,3-propanediamine, 1,4-butanediamine, and 1,3-butanediamine, as well as substituted secondary derivatives thereof.

As was previously mentioned, hydroxy-terminated polyacetals may also be used as polyols in accordance with this invention. These may be prepared, for example, by the reaction of formaldehyde or other suitable aldehyde with a dihydric alcohol or an alkylene oxide such as those previously described.

In order to prepare a rigid polyurethane product, the organic polyisocyanate is reacted with the polyol component optionally in the presence of a blowing agent and preferably a catalyst.

Blowing agents which may be employed in the present invention are well known to those skilled in the art. Representative blowing agents include water, fluorocarbons such as trichloromonofluoromethane, 1,1,1-trichloro-2,2,2-trifluoroethane, tetrafluoromethane, bromotrifluoromethane, chlorotrifluoromethane, dibromodifluoromethane, trichlorethylene, chloroform, carbon tetrachloride and low boiling hydrocarbons such as butane, pentane and hexane. Included are the blowing agents disclosed in U.S. Pat. No. 3,922,238.

Catalysts are also preferably employed. Catalysts which may be used include organometallic catalysts such as dibutyltin dilaurate, dibutyltin dioctoate, stannous dioctoate, lead octoate, and cobalt naphthenate; tertiary amine catalysts such as, triethylenediamine, 1,3,5-tris(3-dimethylaminopropyl)-s-hexahydrotriazine; and other catalysts customarily used in the preparation of polyurethane foams.

Other additives may also be included in the foam formulations. Included are surfactants such as the silicone surfactants, e.g., polyoxyalkylene-polyalkylsiloxane, and flame retardants such as tris(2-chloroethyl)-phosphate.

The examples which follow will provide a detailed description of how to make and use the subject polyols, but are not intended to limit the scope of the invention. The parts referred to in the examples are by weight and the temperatures are in degrees centigrade unless otherwise designated.

EXAMPLES 1-9

All N-(2-hydroxyalkyl)-aniline compositions were prepared in a stainless steel autoclave. The procedure consists of charging into a clean reactor, an catalyst and as the initiator, liquid N-(2-hydroxyalkyl)-aniline. The reactor was then purged with nitrogen and then heated to the desired temperature. The autoclave was vented to 0 PSIG, sealed and the contents stirred for 30 minutes. The oxide was added over seven hours at less than 90 PSIG at the specified temperature. After reacting at the indicated temperature for three hours the product was cooled to 60° C. before discharging. The workup consisted in treating the crude polyol with an absorbent to remove the alkaline catalyst and removal of any trace of volatiles by distillation under reduced pressure. The amine based polyol was then submitted for analytical determination of hydroxyl number, total and tertiary amino nitrogen content, percent of water and percent of residual sodium and potassium. Refractive index and viscosity of the polyols in cps were determined at 25° C. in the laboratory.

Oxyalkylation of N-(2-hydroxypropyl)-aniline or N-(2-hydroxyethyl)-aniline using propylene oxide or ethylene oxide, with potassium hydroxide as the catalyst in amounts of 0.4 percent, 0.8 percent, 2.38 percent and 4.88 percent based on total charge at 150° C. are shown in Table I. Also included are results obtained at 175° C. using 4.88 percent potassium hydroxide.

The data in Table I shows that if the teachings described herein are followed, it is possible to prepare low viscosity aromatic amine polyols by oxyalkylation of N-(2-hydroxyalkyl) aniline resulting in a product that may be used in the preparation of polyurethane products as well as nonionic and ionic surfactants. The data shows that increasing the catalyst level from 0.4 to 4.88 percent at 150° C. decreases the amount of tertiary amino containing material in the product from 34 to 7.6 percent. This further indicates the need for the proper level of catalyst to effect the chain extension and to obtain the novel amino polyols having low viscosity and terminated by hydroxyl and secondary amine function.

In the reaction product, low viscosity at 25° C. usually below 300 cps is apparent. These low viscosities result because the adducts produced have unsymmetric structures as is suggested by the data comparing the total amino content with the tertiary amino content. The difference between the total amino nitrogen and tertiary amino nitrogen is high indicating less than 10 percent of the tertiary amino-containing material in the product. The amount of the tertiary amino-containing material in the polyol increases when lower levels of potassium is used.

As the level of potassium hydroxide used in the polyol synthesis increases, the amount of tertiary amino nitrogen decreases and the difference between the total amino nitrogen and the tertiary amino nitrogen increases indicating a tertiary amino nitrogen content of less than 10 percent in the final product. These properties substantiate compound formation with secondary amino nitrogen and hydroxyl function which when reacted with an organic isocyanate results in compounds having urea and urethane groups and thus useful in producing polyurethane products and nonionic and ionic surfactants.

TABLE I

| | SELECTIVE OXYALKYLATION OF N—(2-HYDROXYALKYL)-ANILINE | | | | | | |
|---|---|---|---|---|---|---|---|
| | Example | | | | | | |
| | 1 | 2 | 3 | 4 | 5 | 6 | 7 |
| Initiator | N(2-hydroxy-propyl)-aniline | N(2-hydroxy-propyl)-aniline | N(2-hydroxy-propyl)-aniline | N(2-hydroxy-propyl)-aniline | N(2-hydroxy-propyl)-aniline | N(2-hydroxy-propyl)-aniline | N(2-hydroxy-propyl)-aniline |
| Composition Molecular Weight | 310.5 | 310.5 | 310.5 | 310.5 | 310.5 | 310.5 | 307.6 |
| Reaction Conditions | | | | | | | |
| Moles PO/Moles initiator | 2.75 | 2.75 | 2.75 | 2.75 | 2.75 | 2.75 | 2.70 |
| Oxide adduct °C.-Hrs. | 150°-7 | 150°-7 | 150°-7 | 150°-7 | 150°-7 | 175°-7 | 150°-2 |
| Reaction °C.-Hrs. | 150°-3 | 150°-3 | 150°-3 | 150°-3 | 150°-3 | 175°-3 | 150°-2 |
| % KOH | 0.4 | .88 | 2.38 | 4.88 | 4.88 | 4.88 | 4.88 |
| Stripped Product Analyses | | | | | | | |

TABLE I-continued

SELECTIVE OXYALKYLATION OF N—(2-HYDROXYALKYL)-ANILINE

| | Example | | | | | | |
|---|---|---|---|---|---|---|---|
| | 1 | 2 | 3 | 4 | 5 | 6 | 7 |
| % Total Amino Nitrogen | 5.76 | 4.48 | 4.44 | 4.75 | 4.87 | 4.31 | 4.85 |
| % Tertiary Amino Nitrogen | 1.94 | 1.34 | 0.81 | 0.39 | 0.41 | 0.33 | 0.45 |
| Viscosity cps. at 25° C. | 500 | 318 | 381 | 200 | 195 | 198 | 540 |
| % tertiary Nitrogen in Product, calculated as: | 34 | 30 | 18 | 8 | 8.4 | 7.6 | 9.0 |

$$\frac{\%\ \text{tertiary amino nitrogen}}{\%\ \text{total amino nitrogen}}$$

The embodiments of the invention in which an exclusive privilege or property is claimed are defined as follows:

1. An oxyalkylated amine having a secondary amino nitrogen and hydroxy functional groups and a viscosity of less than about 540 cps at 25° C. prepared by reacting N-(2-hydroxyalkyl)-aniline with propylene oxide, ethylene oxide or mixtures thereof in the presence of from about 2.38 to about 5 percent based upon total charge of a catalyst at a temperature of from about 150° C. to about 200° C.

2. The oxyalkylated aromatic amine of claim 1 prepared at an elevated temperature in the presence of an alkali metal hydroxide.

3. A process for preparing an amino polyol having a viscosity less than about 540 cps at 25° C. comprising an oxyalkylated aromatic amine having a secondary amino nitrogen and hydroxy functional groups and less than about 18 percent tertiary amino nitrogen consisting essentially of oxyalkylating an N-(2-hydroxyalkyl)-aniline with propylene oxide, ethylene oxide or a mixture of both oxides in the presence of from about 2.38 to about 5 percent based upon total charge of an alkali metal hydroxide at a temperatue of from about 150° C. to about 200° C.

4. The process of claim 3 wherein the alkali metal hydroxide is potassium hydroxide.

5. A polyol blend comprising a polyoxyalkylene polyether polyol and the aromatic amine of claim 1.

6. A process for preparing a polyurethane foam comprising reacting an organic polyisocyante with a polyol as defined in claim 1.

* * * * *